United States Patent [19]
Phillips

[11] Patent Number: 5,387,246
[45] Date of Patent: Feb. 7, 1995

[54] PROSTHETIC SKI LEG

[76] Inventor: Van L. Phillips, 5499 Maravillas, Rancho Santa Fe, Calif. 92067

[21] Appl. No.: 17,245

[22] Filed: Feb. 12, 1993

Related U.S. Application Data

[63] Continuation-in-part of Ser. No. 977,654, Nov. 17, 1992, which is a continuation of Ser. No. 337,374, Apr. 13, 1989, Pat. No. 5,181,932, and a continuation-in-part of Ser. No. 662,783, Feb. 28, 1991, Pat. No. 5,290,319.

[51] Int. Cl.⁶ .............................................. A61F 2/66
[52] U.S. Cl. ...................................... 623/56; 623/55; 623/53; 623/27; 36/118
[58] Field of Search ................ 623/27, 55, 56, 53; 36/118

[56] References Cited

U.S. PATENT DOCUMENTS

| | | |
|---|---|---|
| 61,780 | 1/1867 | Watson . |
| 2,475,372 | 7/1949 | Catranis . |
| 3,747,235 | 7/1973 | Post ................... 36/118 X |
| 3,784,988 | 1/1974 | Trumpler ................. 623/35 |
| 3,982,280 | 9/1976 | Asbelle et al. ............ 623/55 X |
| 4,328,594 | 5/1982 | Campbell et al. . |
| 4,461,103 | 7/1984 | Annovi ................. 36/118 X |
| 4,547,913 | 10/1985 | Phillips . |
| 4,570,926 | 2/1986 | Ensmerger .............. 623/32 X |
| 4,617,920 | 10/1986 | Carsalade ............... 623/43 X |
| 4,721,510 | 1/1988 | Cooper et al. . |
| 4,822,363 | 4/1989 | Phillips . |
| 4,865,612 | 9/1989 | Arbogast et al. . |
| 4,959,073 | 9/1990 | Merlette . |
| 4,994,086 | 2/1991 | Edwards . |
| 5,007,938 | 4/1991 | Prahl . |
| 5,019,109 | 5/1991 | Voisin ................... 623/49 |
| 5,037,444 | 8/1991 | Phillips . |
| 5,112,356 | 5/1992 | Harris et al. . |
| 5,116,381 | 5/1992 | Palfray . |
| 5,116,384 | 5/1992 | Wilson et al. . |
| 5,156,631 | 10/1992 | Merlette . |
| 5,181,932 | 1/1993 | Phillips . |
| 5,181,933 | 1/1993 | Phillips . |

FOREIGN PATENT DOCUMENTS

| | | |
|---|---|---|
| 807214 | 6/1951 | Germany . |
| 883321 | 7/1953 | Germany . |
| 0022172 | of 1898 | United Kingdom ............. 623/56 |
| 2092451 | 8/1982 | United Kingdom . |
| 2202448 | 9/1988 | United Kingdom . |
| 0251758 | 9/1969 | U.S.S.R. .................... 623/27 |
| 8800815 | 7/1986 | WIPO . |
| 8909036 | 10/1989 | WIPO . |

Primary Examiner—David H. Willse
Attorney, Agent, or Firm—Knobbe, Martens, Olson & Bear

[57] ABSTRACT

A prosthetic ski leg designed to be attached to a stump of a wearer which has a pair of conventionally shaped binding mounts for stepping into ski bindings. The prosthetic ski leg includes several structural members having resilient properties for storing and releasing energy. The ankle portion functions as a primary bending load member and may be formed to control the inherent stiffness. A secondary stiffness member may be provided to contribute a level of stiffness or to limit the range of motion. An air bag having a pressure adjustment may be disposed between the secondary stiffness member and the ankle portion to increase or decrease the amount of contribution of the secondary stiffness member. A shock cord may also be provided to adjust the stiffness of the ski leg by varying the elasticity and length of the shock cord.

33 Claims, 7 Drawing Sheets

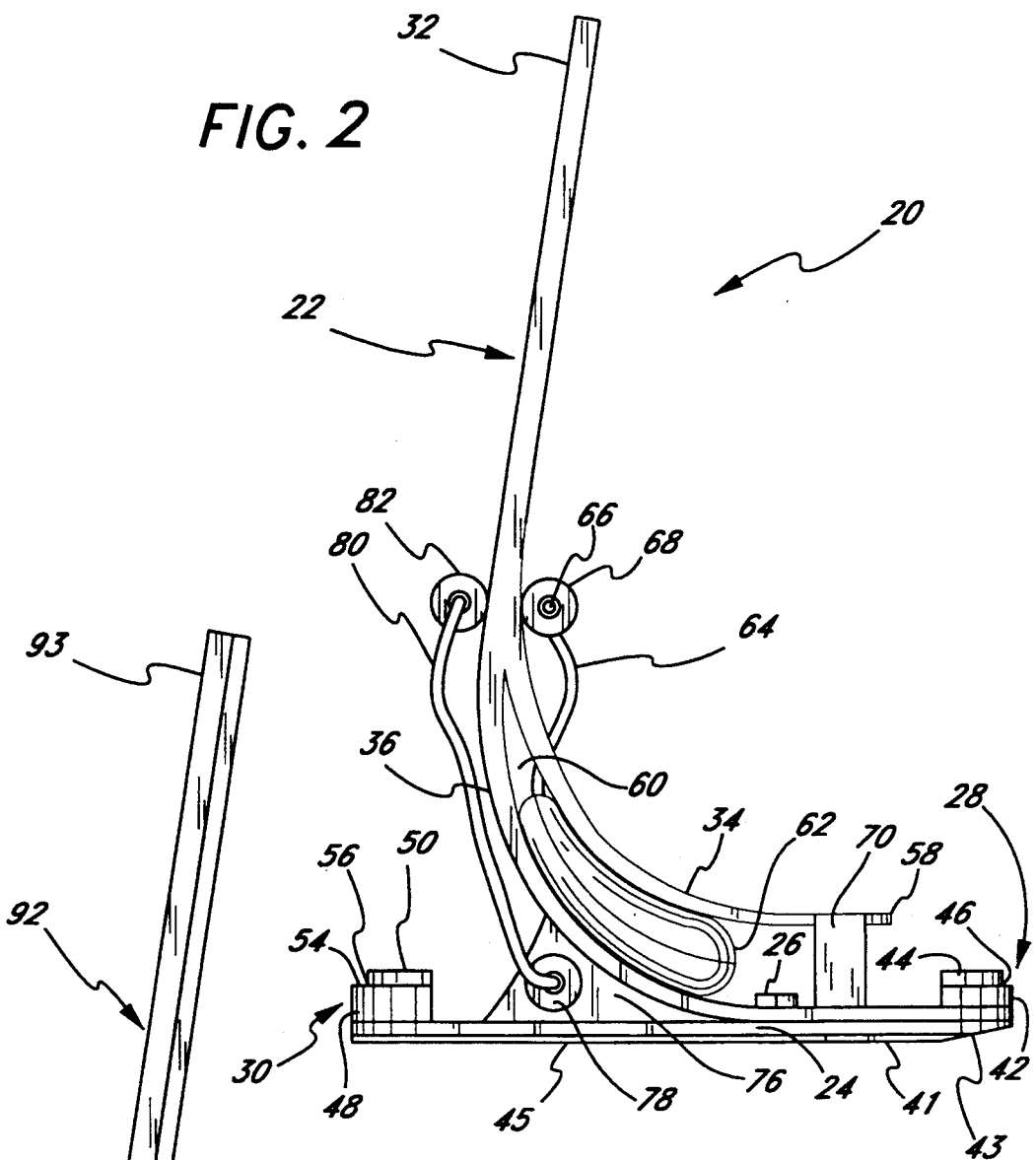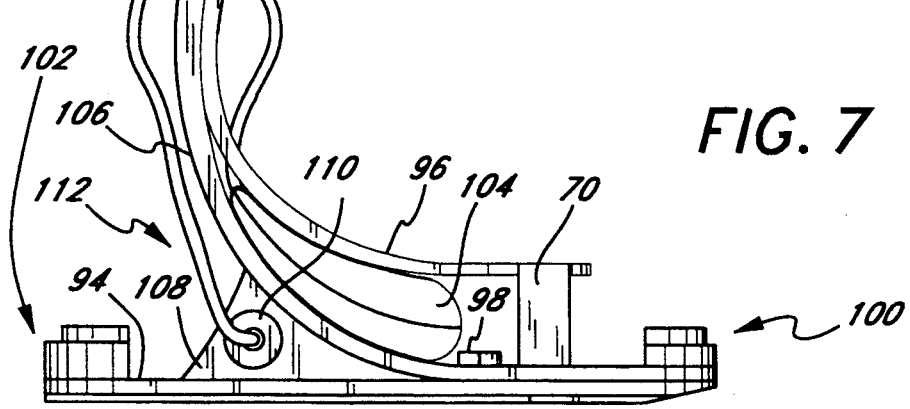

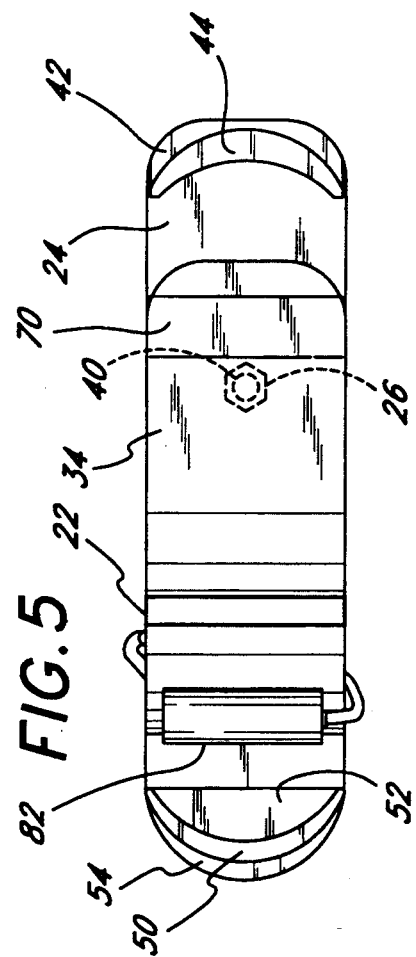
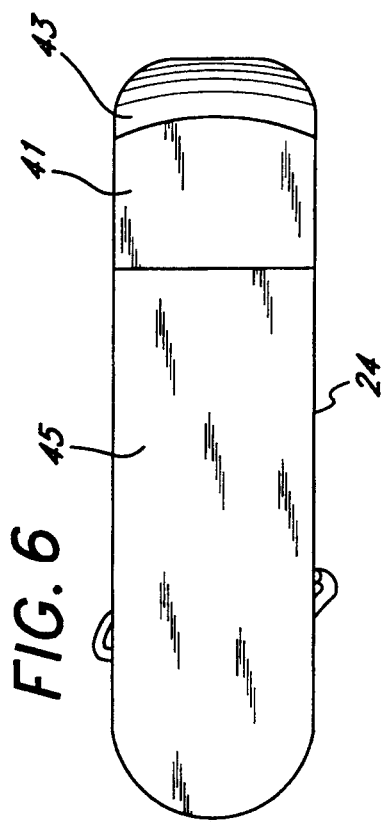
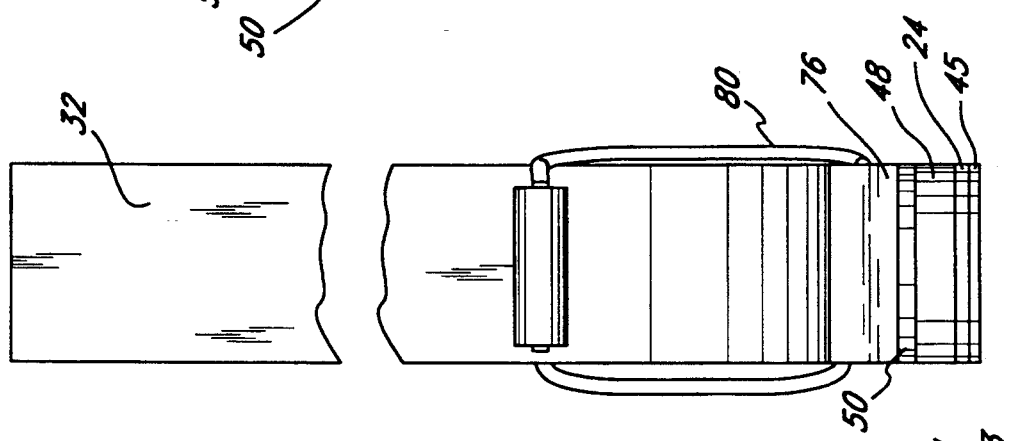
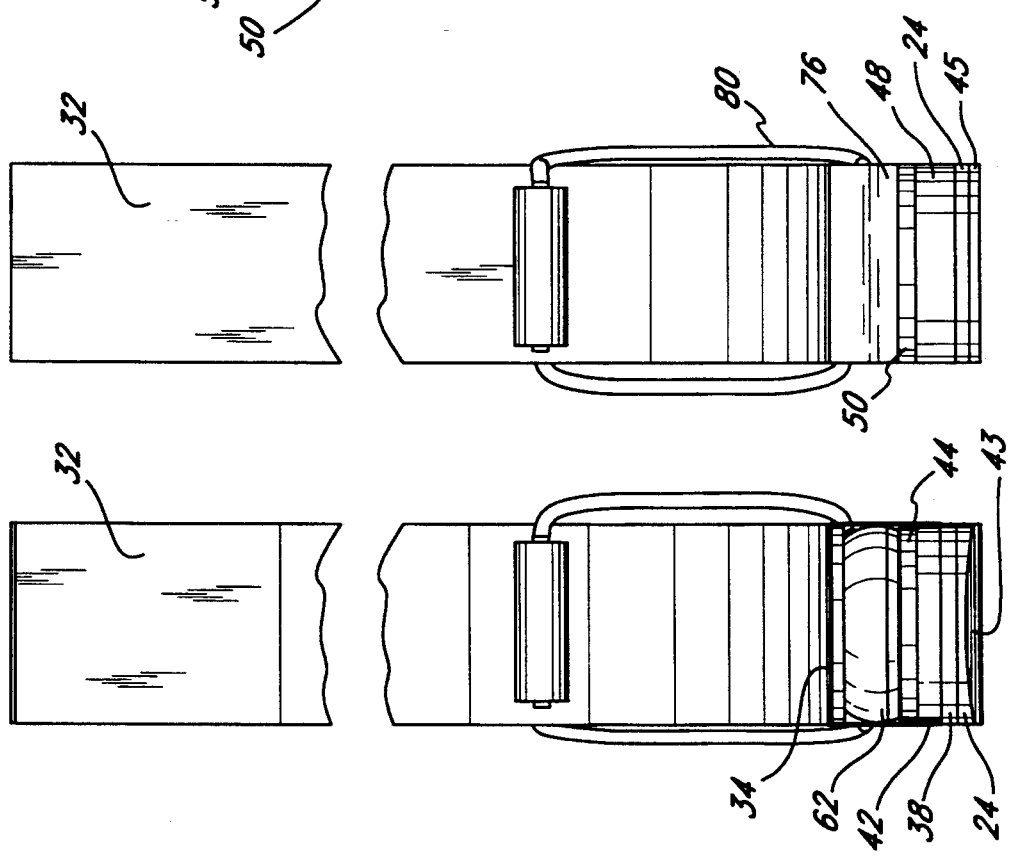

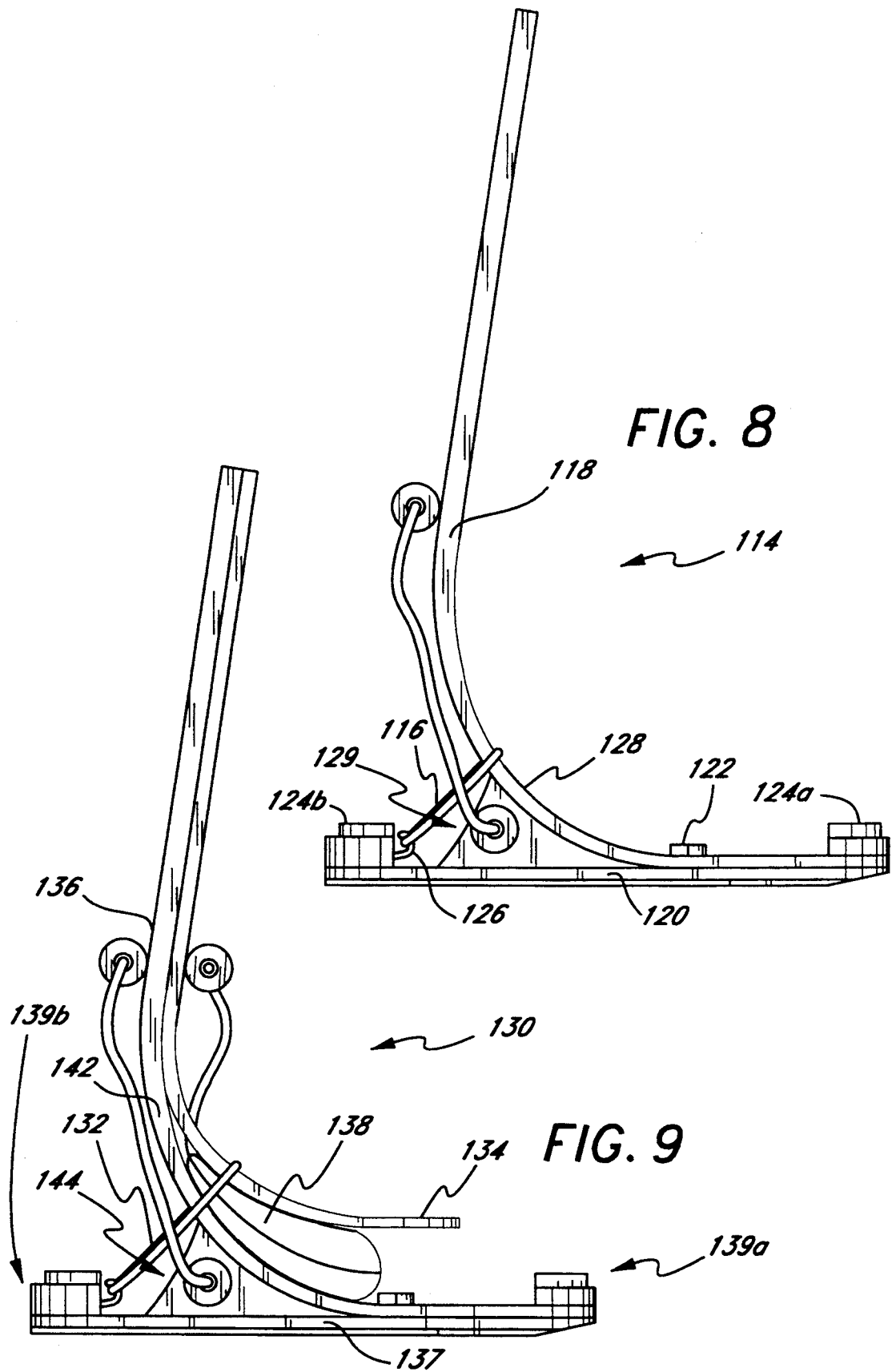

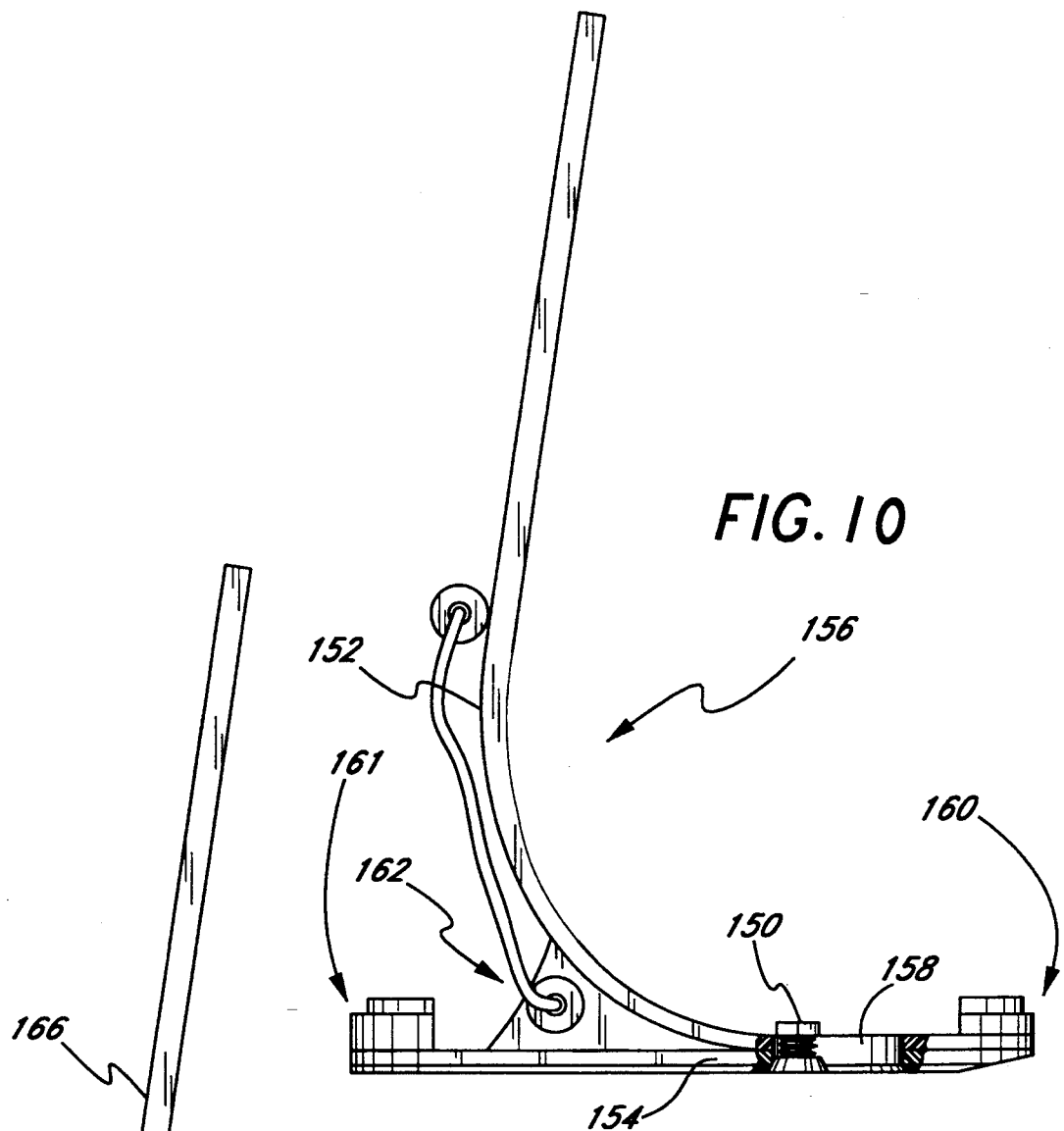

PROSTHETIC SKI LEG

This application is a continuation-in-part of U.S. application Ser. No. 07/977,654, filed Nov. 17, 1992, pending, which is a continuation of U.S. Ser. No. 337,374, now U.S. Pat. No. 5,181,932, issued Jan. 26, 1993, filed Apr. 13, 1989. This application is also a continuation-in-part of U.S. application Ser. No. 07/662,783, filed Feb. 28, 1991, now U.S. Pat. No. 5,290,319.

BACKGROUND OF THE INVENTION

1. Field of the Invention

The present invention pertains to an improved prosthetic device for active amputees, and more particularly to an improved prosthetic leg for use in skiing.

2. Description of the Related Art

In the past 10 years there have been numerous technological advances in the field of prosthetics. In particular, an amputee has a wide range of selection of prosthetic legs to choose from. Along with the general type of prosthesis for walking, there has been a concurrent demand for prostheses which enable an amputee to lead a more active lifestyle. Much effort has been made in the industry to develop products for hiking, running, climbing, and even such rigorous sports as basketball.

Unfortunately, the advances in prostheses have not produced any developments for an amputee who prefers skiing as a recreation or sport. Currently, an amputee has the option of fitting a prosthesis or, in some instances, the lower portion of a stump into a conventional ski boot and then to the ski, or simply skiing one legged with poles having ski runners. For an amputee to fit a ski boot onto the stump is quite awkward as the boot may weigh up to four or five pounds. Walking with such a bulky and rigid boot under normal circumstances would also be extremely difficult for an amputee. The alternative to wearing the boot is to remove it and carry it to and from the ski slopes, which is inconvenient.

Skiers prefer to have various levels of flexibility in the skis, bindings and boots when facing different terrains. In general, it is better to have more flexibility on the advanced slopes with many moguls where the skier develops more inertia so that the ski will have a greater range of motion and more closely follow the contours. Likewise, it is desirable to have a stiffer or less flexible ski/boot combination when descending a less rigorous, flatter run to avoid excessive back and forth wobbling. All ski boots are made fairly rigid and designed to fit tightly to one's leg, with a correspondingly limited range of motion. Ski boots are not intended to be used by amputees, and correspondingly, prosthetic devices are not suitable for fitting precisely into ski boots. Strapping a boot onto the end of a prosthetic device is a relatively poor compromise which does not enable an amputee to fully utilize the range of motion needed to ski varied terrains.

Every four years, the Paralympics follows the regular Olympics, with the competition being just as fierce, although not as highly publicized. Downhill amputee ski racers and their sponsors have for years attempted to get an edge on the competition by developing better skiing equipment for amputees. Regrettably, even given the high profile, financing and concentrated effort of such sportsmen and designers, the technology has not advanced much beyond the conventional boot method.

The present invention provides a new and improved prosthetic leg for use in skiing, which overcomes the aforementioned deficiencies.

SUMMARY OF THE INVENTION

In accordance with the present invention, a prosthetic ski leg is adapted to be directly attached to conventional bindings of a ski. An upper portion of the prosthetic ski leg attaches directly to a stump connector of various configurations. The lower region of the prosthetic ski leg includes front and rear binding mounts shaped and sized to fit within conventionally sized ski bindings in precisely the same manner as a typical ski boot. The prosthetic ski leg of the present invention is manufactured using extremely light weight and strong materials so that an amputee is freed from the cumbersome aspects of fitting a typical ski boot onto a prosthesis. In addition, the prosthetic ski leg is characterized by an instantaneous response to imposed loads and correspondingly instantaneous delivery of stored energy. Furthermore, the amputee skier may tackle a wide variety of ski run terrains and may easily and precisely adjust the stiffness and spring characteristics according to the terrain.

In accordance with the preferred embodiment, the prosthetic ski leg comprises a leg member, a sole member adapted to be connected to the bottom of the leg member, and front and rear binding mounts attached at generally toe and heel locations, respectively. The leg member comprises a generally vertical upper rigid portion suitable for attaching to various stump connectors, a flexible curvilinear ankle portion, a horizontal foot portion having one or more apertures for receiving a connector to attach the leg member to the sole member, and a toe binding mount fastened to the forward upper surface. The sole member is generally a straight, planar member which substitutes for the bottom of a conventional ski boot. The sole member comprises a heel portion on which the heel binding mount fastens to the upper surface, a central portion, a lower toe portion having a corresponding aperture for the connector between the sole member and the leg member, a front lower taper, and a bottom release pivot plate affixed to the underside of the lower toe portion.

As was stated above, the front and rear binding mounts are spaced apart a distance within a range in which conventional ski bindings may be adjusted to properly receive the binding mounts. Thus, after attaching the leg member to a connector and the connector to the stump, the amputee need only position the front binding mount within the toe binding and step downwards so that the rear binding mount snaps into the heel binding, whereupon the amputee is ready to ski. Likewise, the heel binding may be released by any of several conventional means to release the rear binding mount and the amputee may step out of the ski bindings. Also, the heel binding typically having a spring-loaded mechanism, the prosthetic ski leg performs exactly like a conventional ski boot when the skier falls as the rear binding mount easily pops out of the heel binding when the torsional force is sufficient to overcome the spring load. A wide variety of cosmetic covers may be incorporated into the prosthetic ski leg to disguise the structural members therein and protect other skiers in case of a collision. Once the amputee steps out of the ski, the prosthetic ski leg performs adequately as a prosthetic foot, and is certainly preferable to a cumbersome ski boot.

In accordance with the principles of the present invention, the underside of the prosthetic ski leg is provided with a flat release pivot plate proximate the front end of the sole member so that the ski leg may easily pivot out of the ski bindings in case of a fall. The rest of the underside of the sole member may be covered with urethane or other traction material to facilitate walking across snow and ice. Thus, the amputee skier using the prosthetic ski leg of the present invention may readily remove the skis and temporarily exit the ski slopes for a warming hut or lodge whereupon the skier easily steps back into the skis and continues the day's skiing.

An important aspect of the present invention is the capacity to adjust the flexibility of the prosthetic ski leg readily and easily to prepare for descending various levels of ski slopes. One way to adjust the flexibility is the inclusion of an auxiliary or secondary stiffness member which projects from the front face of the leg member. Thus, the secondary stiffness member initially runs parallel to the vertical upper rigid portion and diverges therefrom approximately at the interface between the upper rigid portion and the curvilinear ankle portion, extending forward in a curvilinear path and eventually running parallel with the generally horizontal foot portion of the leg member.

The divergence of the secondary stiffness member from the leg member creates a space therebetween into which a forward bending stiffness adjustor is disposed. The forward bending stiffness adjustor may comprise an inflatable fluid-or gas-filled bag which interacts with the upper surface of the curvilinear ankle portion and also with the lower surface of the secondary stiffness member. As the prosthetic ski leg bends forward about the curvilinear ankle portion, the secondary stiffness member contacts the forward bending stiffness adjustor to add a measure of stiffness to any further bending.

The size and shape of the forward bending flexibility adjustor determines the timing and level of stiffness which is added to the inherent stiffness of the ankle portion of the prosthetic ski leg. In one embodiment, the forward bending stiffness adjustor is a solid or resilient material which contacts both the ankle portion and secondary stiffness member when the prosthetic ski leg is in a relaxed state, and any forward bending whatsoever of the prosthetic ski leg is immediately resisted by not only the stiffness of the ankle portion but also by the secondary stiffness member. Therefore, providing an air bag as a forward bending stiffness adjustor allows the stiffness to be adjusted continuously by modulating the internal pressure supplied to the air bag. The air bag provides a gradual dynamic transition during loading of the prosthetic ski leg.

It should be understood that the present invention is not limited to prosthetic ski legs having either a secondary stiffness member or a forward bending stiffness adjustor, and the ankle may be selected to provide a desired stiffness for a range of slope difficulties. Moreover, the prosthetic ski leg may incorporate a secondary stiffness member without an interactive forward bending stiffness adjustor, such as an air bag, in which case the secondary stiffness member would act alone, not adding significant stiffness until the leg was bent forward far enough for the secondary stiffness member to contact the foot portion of prosthetic ski leg.

The preferred embodiment of the air bags of the present invention may be fabricated in a variety of configurations, including those having multiple chambers and tapered cross sections. Such configurations permit the air bag to be positioned in unusual but useful locations between the structural components of the prosthetic ski leg. In a preferred embodiment, the air bag includes a valve for adjusting the internal pressure and the corresponding feel and performance characteristics of the prosthetic ski leg into which it is incorporated.

In accordance with the principles of the present invention, the secondary stiffness member may be manufactured from the same material as the leg member and may be integral therewith or a separate component. The leg member, sole member and secondary stiffness member are preferably constructed of graphite or, alternatively, the material may be constructed of polymer impregnated superimposed reinforcing laminae such as a chopped or matted fiberglass matrix with a resin hardener. In one embodiment, the secondary stiffness member comprises a separate component running vertically parallel to the upper portion of the leg member and diverging above or at the upper end of the curvilinear ankle portion. In this case, the secondary stiffness member may be attached flush with the leg member or may be spaced therefrom and have a vertical portion of the forward bending stiffness adjustor disposed therebetween so that the entire vertical portion of the prosthetic ski leg has the capacity for stiffness adjustment.

In a further embodiment of the present invention, a shock cord attached proximate the heel binding mount extends around either the leg member or around a secondary stiffness member forward of the leg member to provide a forward bending stiffness adjustment. The shock cord may be fabricated of various materials and may have varying levels of resiliency. For instance, the shock cord may be relatively thick urethane tubing having a predetermined level of resiliency or the shock cord may be a stiffer material such as steel cable. Depending on the distance between the connection at the heel binding mount and the structural member around which the shock cord is looped, and the length of the shock cord, forward bending of the prosthetic ski leg eventually pulls the shock cord taut and increases the forward bending stiffness of the ski leg. When a resilient shock cord is wrapped around the curvilinear ankle portion of the leg member, a certain level of spring stiffness is added to the ski leg while a less resilient steel cable shock cord would actually prevent any further forward bending of the ski leg. Alternatively, looping the shock cord around a secondary stiffness member provides a way other than the aforementioned air bag for bringing the secondary stiffness member into play upon forward bending of the ski leg. Additionally, the shock cord looped around the secondary stiffness member may work in conjunction with an air bag placed between the secondary stiffness member and the leg member to provide an integrated and highly adjustable ski leg. Furthermore, the connection at the heel binding mount may be a simple eye hook which allows the interchangeability of different shock cords even on the ski slope.

In another embodiment of the present invention, the flexibility of the leg member may be adjusted by providing structure for varying the longitudinal position of a connector between the leg member and the sole member. Moving the connector farther forward towards the toe binding mount creates a large moment arm about which the upper rigid portion of the leg member bends. Thus, a larger moment may be applied to the upper rigid portion by the skier and the prosthetic ski leg is thus more flexible, which is generally preferable for rougher terrain. In a preferred configuration, aligned slots in both the leg member and sole member allow the connector to be slid forward or backward to adjust this moment arm. The connector may be any number of fasteners but is preferably a bolt and nut combination which is recessed into the bottom surface of the sole member so as to lie flush therewith. The amputee skier need only loosen the upper nut or bolt head and slide the nut and bolt combination in the desired direction whereupon the connector is refastened and the amputee is ready to ski once again. In an alternative embodiment, a series of through holes may be provided through which the connector passes to vary the level of flexibility of the ski leg.

In a further configuration of the present invention, an arcuate or C-shaped secondary stiffness member having a radius which is smaller than the radius of the curvilinear ankle portion of the leg member may be attached to the approximate center of the ankle portion. In the relaxed state, the upper and lower ends of the arcuate-shaped secondary stiffness member extends forward or diverge from the curvilinear ankle portion. Thus, when the ski leg is in a state of forward bending, the diverging ends of the stiffness member contact the leg member and provide further resistance to bending at that time. The arcuate-shaped secondary stiffness member may also be used in conjunction with an air bag or with a shock cord as described above.

In accordance with the advantageous features of the present invention, the prosthetic ski leg may also be provided with a device for adjusting the stiffness in rearward bending. Such a device may include a resilient wedge-shaped member interposed between the underside of the curvilinear ankle portion and the upper surface of the sole member. A rearward bending stiffness adjustor is provided within the resilient wedge for adjusting the amount of stiffness imparted on the leg member when the skier leans backward. Such a stiffness adjustor is preferably a cylindrical air bag extending transversely through the resilient wedge in the approximate center. The cylindrical air bag may be inflated or deflated to adjust the level of stiffness underneath the curvilinear portion. Additionally, the inflatable bag may be filled with other fluids as well. Preferably, a valve is provided on one side of the cylindrical air bag to allow the amputee to readily adjust the pressure within the bag and thus the stiffness in rearward bending of the prosthetic ski leg.

In accordance with an alternative embodiment of the present invention, the leg member may be substantially straight and attached at its lower end to the upper surface of the sole member. A mechanism for supporting the cantilevered leg member in forward and rearward bending are provided. Such a mechanism may include fluid- or gas-filled shock absorbers pivotably attached to either side of the leg member and angled downward to attach to the upper surface of the sole member. Such shock absorbers may be adjustable by the amputee on the slope and thus provide a stiffness adjusting means for different terrains. In another configuration, the vertically disposed leg member may be surrounded by a pair of air bags which are in turn vertically braced by a pair of L-shaped brackets having lower portions attached to the sole member. Thus, the leg member imparts forces on the air bags and against the L-shaped brackets when being bent forward or backward. Again, the air bags may have separate or common valve for adjusting the pressures therein. Furthermore, the air bags may be replaced by resilient cushions or bumpers to provide a relatively fixed level of flexibility to the prosthetic ski leg.

Thus, the prosthetic ski leg of the present invention provides several substantial advantages over the devices of the prior art.

BRIEF DESCRIPTION OF THE DRAWINGS

FIG. 2 is a side elevational view of the prosthetic ski leg of FIG. 1;

FIG. 3 is a front elevational view of the prosthetic ski leg of FIG. 1;

FIG. 4 is a rear elevational view of the prosthetic ski leg of FIG. 1;

FIG. 5 is a top plan view of the prosthetic ski leg of FIG. 1;

FIG. 6 is a bottom plan view of the prosthetic ski leg of FIG. 1;

FIG. 7 is a side elevational view of an alternative embodiment of the prosthetic ski leg having a separate secondary stiffness member and an air bag as a forward bending stiffness adjustor;

FIG. 8 is a side elevational view of another alternative embodiment of the prosthetic ski leg having a shock cord as a forward bending stiffness adjustor;

FIG. 9 is a side elevational view of another alternative embodiment of the prosthetic ski leg having an air bag and a shock cord wrapped around a secondary stiffness member;

FIG. 10 is a side elevational view of a further alternative embodiment of the prosthetic ski leg showing a longitudinally adjustable connector between a leg member and a sole member;

FIG. 11 is a side elevational view of a further alternative embodiment of the prosthetic ski leg having an arcuate or C-shaped secondary stiffness member;

DESCRIPTION OF THE PREFERRED EMBODIMENTS

Figure 1:
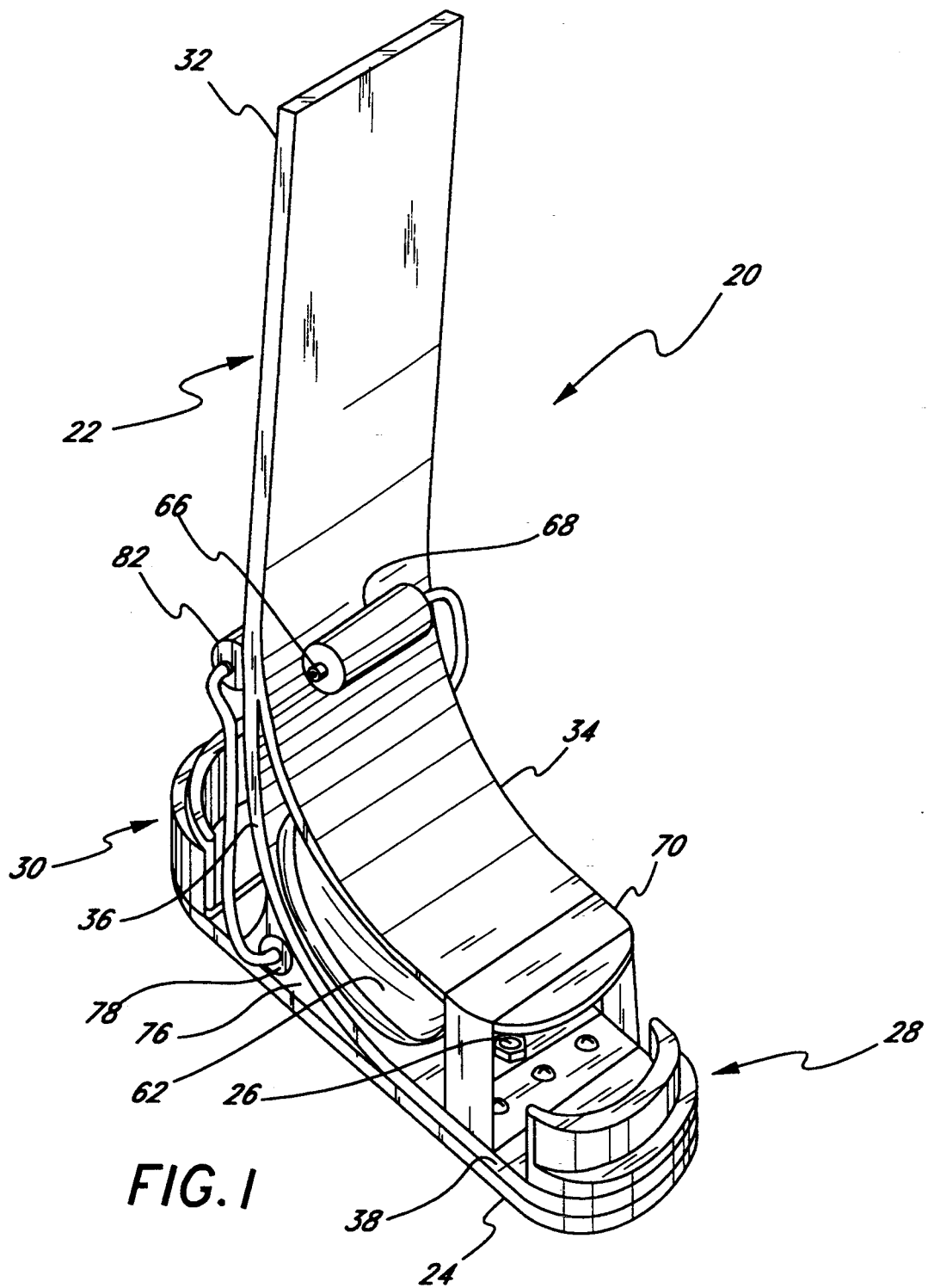
FIG. 1 is a perspective view showing a preferred embodiment of the prosthetic ski leg of the present invention.

FIG. 1 shows a preferred embodiment of the prosthetic ski leg 20 of the present invention. The prosthetic ski leg 20 generally comprises a leg member 22 which transitions from an upright orientation at the top to a horizontal orientation. A connector 26, such as a bolt and nut combination, passes through aligned apertures 40 (FIG. 5) to secure the leg member 22 and sole member 24 together. A pair of clips in the form of a toe binding mount 28 and a heel binding mount 30 provide the capability of attaching the prosthetic ski leg 20 into the bindings of a typical downhill ski (not shown). At the top end of the leg member, an upper rigid portion 32 provides a sturdy attachment member to which a connector (not shown) adapted to fit to a stump of an amputee may be fastened. Such connectors are well-known in the art and will not be described further herein. A cosmesis (not shown) or cosmetic cover may be provided to disguise the structural components of the prosthetic ski leg 20. Such a cosmesis may be designed to closely resemble a typical ski boot.

Once the prosthetic ski leg 20 has been attached to the stump of an amputee, the ski leg may readily snap into the bindings of a ski with the same ease as with a conventional ski boot. In this regard, the toe binding mount 28 and heel binding mount 30 are spaced apart a sufficient distance to be within the typical linear adjustment range of downhill ski bindings. The adjustment of bindings can normally be done with a screwdriver, and thus the prosthetic ski leg 20 of the present invention can easily be fitted to any pair of downhill skis. In addition, the mounts 28, 30, as well as other portions of the sole member 24, may be adapted to conform to any conventional ski boot bindings, now existing or later developed, and should not be construed to be limited to the particular configuration shown.

In the embodiment shown in FIGS. 1-6, the prosthetic ski leg 20 includes an auxiliary or secondary stiffness member 34 integral with the leg member 22; although the invention is not limited to such an embodiment. In the alternative, the secondary stiffness member 34 may be detachable so that members of varying stiffness may be adjustably mounted on the leg member 22. The leg member 22 comprises the aforementioned upper rigid portion 32, a curvilinear ankle portion 36 and a horizontal foot portion 38 in addition to the secondary stiffness member 34.

As shown in FIG. 2, the upper rigid portion is oriented at a slight angle, desirably between 5°-15°, and preferably 10°, and in a line which would intersect the flat sole member 24 rearward from a centerline. Thus, the overall shape of the prosthetic ski leg 20 substantially mirrors the shape of a typical ski boot, which is also slightly angled forward at the shin region. In order to fit a prosthetic ski leg 20 of the present invention to a particular amputee, the upper rigid portion 32 is severed at a distance which will be sufficient to meet the stump connector of the amputee and the prosthetist, therefore, first determines the length of the upper rigid portion and selects an off-the-shelf leg member of the appropriate height or customizes one by simply cutting the rigid portion to height.

Sole Member and Binding Mounts

In one embodiment, the sole member 24 is approximately a foot long and the curvilinear ankle portion 36 extends upward approximately 8" above the sole member. The upper rigid portion 32 extends from the ankle portion 36 to the stump of the amputee, such distance varying from patient to patient.

As seen in FIG. 6, the bottom of the sole member 24 comprises a front pivot plate 41 terminating in a forward taper 43 and a rear traction region 45. The front pivot plate 41 may be constructed of a suitably hard smooth material, such as aluminum or hard self-lubricating material in order to facilitate release of the prosthetic ski leg 20 from the ski bindings in case of a fall. Such a flat pivot plate is a uniform feature in ski boots. Rearward of the pivot plate 41, the traction region 45 enables an amputee to remove the ski and have a measure of stability when walking on ice and snow, not to mention dry surfaces. The traction region 45 may be a suitable tough urethane material or other typical boot material well-known in the art.

With reference to FIG. 2, the toe binding mount 28 and heel binding mount 30 comprise stops against which a toe and heel binding combination bias the prosthetic ski leg 20 onto each ski. The toe and heel binding mounts 28, 30 thus faithfully recreate the front and rear binding clips of a conventional ski boot which shape is relatively uniform in the industry.

The toe binding mount 28 includes a lower horizontal flange portion 42 and an upstanding arcuate binding stop 44 slightly inset from the forward edge of the horizontal flange portion so as to create a step 46 for receiving the toe binding. The lower horizontal flange portion 42 is rigidly attached to the top surface of the foot portion 38 of the leg member and terminates flush with the forward end of the foot portion. The arcuate shape of the upstanding stop 42, shown in FIG. 5, contacts a correspondingly shaped toe binding which fits closely on the step 46 formed between the stop and lower flange portion 42.

The heel binding mount 30 (FIGS. 2 and 5) comprises an arcuate step body 48, an upper arcuate lip 50 and an inner horizontal flange 52 for attaching the heel binding mount to the sole member. The step body 48 includes an upper surface 54 from which the arcuate lip 50 extends further upward and which is slightly recessed from the rearward facing arcuate side to form a step 56 for the heel binding. Thus, the upper surface 54 of the step body 48 in combination with the rearward surface of the arcuate lip 50 define the step 56 which closely contacts the heel binding. Both the toe binding 28 and heel binding mount 30 are bonded and/or fastened with bolts, for example, to the prosthetic ski leg 20. Any fasteners extending through the leg member 22 or sole member 24 are recessed to lie flush with the bottom surface of the sole member. The toe and heel binding mounts 28, 30 may be constructed from chopped, molded graphite, fiberglass laminate, aluminum or any other suitably rigid and lightweight material.

Leg Member

As seen in FIG. 2, the upper rigid portion 32 of the leg member 22 provides a stiff impediment to bending about that region, whereas the curvilinear ankle portion 36 is thinner and thus a majority of the bending of the ski leg 20 occurs there. Specifically, the bending of the leg member 22 occurs between the upper part of the curvilinear ankle section and the point at which the connector 26 mounts the leg member 22 to the sole member 24. Substantially all of the stiffness in bending of the prosthetic ski leg, therefore, is provided by the primary stiffness member of the curvilinear ankle portion 36. The skier thus applies a bending moment to the primary stiffness portion of the ankle when changing the angle the upper rigid portion 32 makes with the sole member 24.

It should be understood that the present invention is not limited to prosthetic ski legs having a secondary stiffness member 34, and leg members 22 may be selected for a desired level of stiffness and spring-response depending primarily on the thickness in the ankle region 36. Thus, due to the advantageous modular construction of the prosthetic ski leg 20 provided by the standard connector 26, various size and shapes of leg members 22 may be supplanted for one another depending on a particular amputee's skiing proficiency. For instance, if an amputee is a beginner skier, a relatively rigid ankle portion 36 is desired to reduce the amount of wobbling forward and backward which the skier would experience. Furthermore, any number of leg members 22 may be interchanged on the same sole member 24 due to the provision of the standard connector 26. Although a coarse stiffness adjustment of the ski leg 20 of the present invention is realized by the modular construction, even greater fine tuning or control of the stiffness and/or flexibility of the ski leg is attained by various secondary stiffness members and adjustors, as will be described in more detail below.

Secondary Stiffness Member

Referring again to FIGS. 1 and 2, the aforementioned secondary stiffness member 34 diverges from approximately the top end of the ankle portion 36 of the leg member to curve downward and forward and terminate in a generally horizontal plane at the forward tip 58. The integral construction eliminates material and additional connectors thus saving weight. The radius of curvature of the stiffness member 34 is preferably smaller than the radius of curvature of the ankle portion 36 so that a space 60 is formed therebetween. The space 60 is varied by changing the radius of curvature of the secondary stiffness member 34, thus determining the angle of bend of the leg member 22 at the point at which the secondary stiffness member contacts the upper surface of the ankle portion and increases the stiffness of the leg 20.

As can be interpreted from FIG. 2, a forward bending of the leg member 22 produces stress in the ankle member 36 up until a point when the secondary stiffness member 34 contacts the upper surface thereof. Prior to the contact between the secondary stiffness member 34 and the ankle portion 36 and/or foot portion 38, the secondary stiffness member realizes no significant imposed load due to the leg member 22 bending. At the instant of contact with between the stiffness member 34 and ankle portion 36 and/or foot portion 38, a greater force is required to bending the leg member 22 farther as the secondary stiffness member is now absorbing some of the bending load. The amount of resistance to bending added by the secondary stiffness member 34 depends on the thickness and material composition of the member which may vary, and a number of combinations of ankle 36 and secondary stiffness member may be made available as off-the shelf versions. Preferably, as shown in FIGS. 1 and 2, the secondary stiffness member 34 is an integral part of the leg member 22, and thus has similar material properties, and also is tapered toward the front tip 58. Advantageously, the front tip 58 contacts the top surface of the ankle portion 36 first and is somewhat more pliable than the remainder of the secondary stiffness member 34 to add only a small stiffness at first which gradually increases as more of the secondary stiffness member comes into play. This non-linear spring response may be tailored to suit an infinite number of situations and individual preferences.

The secondary stiffness member 34 may be utilized to limit the range of motion of the prosthetic ski leg 20 in bending. In this regard, and as described above, the secondary stiffness member 34 may gradually contribute stiffness to the bending up until a point at which it becomes very difficult to bend further. Alternatively, the secondary stiffness member 34 may be constructed of a completely rigid member to provide a sudden stop against any further bending. In this case, the amount of flexibility/stiffness of the prosthetic ski leg 20 depends upon the material and shape of the leg member 22, and specifically the ankle portion 36. Regardless of how suddenly the secondary stiffness member 34 impedes any further bending, the range of motion may be limited to a mere 1° up to 15°, depending on the difficulty of the ski slope.

Advantageously, the materials of the leg member 22 are chosen to provide an energy storing, resilient, spring-like effect. This is necessary because each engagement of the ski leg 20 with the ski slope impresses compression, torsional, and other loads upon the ski leg which must be stored therein and, depending upon the terrain, must be reimpressed upon the slope to force the ski down, preferably into contact at all times with the slope. The contribution of a secondary stiffness member 34 is important in customizing a spring response of the prosthetic ski leg 20. In order to stop further upward flexing of the ski and instead reapply the stored energy back from the ski onto the slope, the secondary stiffness member 34 provides a stop to achieve this desired force reversal. Such upward flexing may occur, for instance, from a skier leaning forward or from forces impressed on the bottom of the ski from uneven slopes. Thus, depending on the shape, material and position of the secondary stiffness member 34, some bending motion is allowed until the ankle reaches a predetermined angle at which point the bending is stopped and the skier can reapply the full force of his or her weight back to the slope.

Prosthesis Construction

The leg member 22 is preferably molded as a unitary component and carefully formed to provide for appropriate absorption of stress imposed thereon. The configuration of the leg member 22 is of utmost importance and the laminates and the polymer or polymers from which the elements are fabricated must be resilient and capable of absorbing the compressive, torsional, and other stresses referred to above, and of restoring the stored energy created by such stresses, in a natural manner, to the impacted ski slope which originally imposed such stresses upon the prosthetic ski leg 20.

It has been found that there is a limited number of polymers capable of sustaining the significant stresses and repetitive loads imposed upon the ski leg 20, particularly in light of the countless numbers of cycles to which the ski leg is subjected during normal skiing conditions. At present, the best materials for the prosthesis are a composite of high strength graphite fiber in a high toughness epoxy thermosetting resin system. There are several reasons for this: high strength; stiffness to weight ratio of graphite as compared to other materials; the almost complete return of input or stored energy; lightweight; high fatigue strength; and minimal creep. As an alternative material, fiberglass/epoxy is a fair choice, but is not as highly recommended as graphite because of lower fatigue strength and higher density. Kevlar is even less desirable due to poor compression and sheer strength, although it is the lowest density of those mentioned.

To achieve the relatively thin construction of the leg member 22, the aforementioned polymers are utilized in conjunction with various laminating materials. Various types and dimensions of fibrous laminae can be utilized to achieve the continuum required by the design of the leg member 22 to complement the stress absorbing and storing characteristics of the polymers in which the fibrous laminae are invented. There is a wide variety of fibrous reinforcements in the form of laminae available, including such inorganic fibers as glass or carbon fibers. These inorganic fibers are customarily provided in taper or sheet form and can be readily superimposed in the mold to permit them to be encapsulated in the selected polymer. It will be obvious to those skilled in the art that, with respect to any embodiment of the present invention, the fibrous reinforcements in the form of laminae plies may be fayed or tapered to accomplish a gradual transition as the number of plies is reduced in any area of the leg member 22.

Stiffness Adjustor

Referring again to FIGS. 1 and 2, a forward bending stiffness adjustor in the form of an air bag 62 is interposed between the secondary stiffness member 34 and ankle portion 36. The air bag 62 has a generally elongated shape which fills the space 60 along a substantial portion of the arcuate surfaces of the secondary stiffness member 34 and ankle portion 36. The air bag 62 may be positioned between these structural elements and fastened with adhesive to prevent any sliding therefrom. Another means for retaining the air bag 62 in place is the provision of bumpers or rails (not shown) on the upper surface of the ankle portion 36. Additionally, one or more restraining straps 70 of suitably tough, flexible material such as impregnated canvas or the like, may be provided. The restraining straps 70 may be operatively attached to the leg member 22 with one or more screws possibly in conjunction with a small rigidifying plate serving as a washer. Optionally, the straps may be releasably attached around the secondary stiffness member 34 through the provision of fasteners, such as Velcro fasteners, or similar expedient. The restraining strap 70 may be appropriately tightened to flatten the air bag 62, thus increasing the contact areas between the structural members and possibly reducing any role of a "high centered" air bag. Moreover, restraining straps may be incorporated at various locations on the prosthetic ski leg 20 to restrict the distance that associated structural members may move from one another. For example, the restraining strap 70 may permit the secondary stiffness member 34 to assist in raising the toe end of the prosthetic ski leg 20 and ski.

The air bag 62 provides a relatively large contact area load connector between the stiffness member 34 and ankle portion 36. Depending on the level of inflation of the air bag 62, the secondary stiffness member comes into contact with the air bag when the ski leg 20 experiences forward bending. Due to the interposition of the air bag 62 in the space 60 the secondary stiffness member 34 comes into play sooner as the air bag provides a surface on which the secondary stiffness member acts. This is because the secondary stiffness member is cantilevered about the point of connection with the leg member 22.

The air bag 62 provides a resistance to bending which is non-linear. In other words, the compression of air or fluid within the bag 62 is initially quite easy but rapidly becomes harder as the bag is compressed further. Of course, inflating the air bag 62 to high pressures reduces the margin of compressibility and causes the secondary stiffness member 34 to come into play at the first instant of bending. However, the secondary stiffness member may be constructed so as to be relatively rigid so that the spring response or additional stiffness is entirely provided by the air bag 62. Of course, there are a variety of possibilities regarding the combination of the secondary stiffness member 34 and relative inflation of the air bag 62, the provision of a valve adjustment, as described below, enabling the skier to assert some control over the performance of the ski leg 20 while on the slopes.

The air bag 62 may be constructed with an internal bladder and may have an external covering (both not shown). The bladder is preferably fabricated from a suitably strong, thin, flexible, moisture and vapor impervious, lightweight material such as a polyurethane produced by J. P. Stevens Elastomerics Company. The bladder may be formed by heat sealing appropriately sized and shaped pieces of material to each other, or by heat stamping which seals as well as cuts the material to shape. Suitable thicknesses of urethane have been found to be 0.01 to 0.02 inches. However, a wide range of thicknesses and materials for the bladder may be utilized in the present invention. Bladder pressures of up to 80 psi have been utilized. The cover may be fabricated of ballistic nylon or similarly strong material to prevent the bladder from exploding under high pressures and to help define the final inflated shape of the bladder. The cover may be formed from separate pieces stitched together at the perimeter of the bladder member, before or after being cut to their desired final shapes. Those skilled in the art will understand that a variety of covered materials and methods of fabrication and assembly thereof may be utilized with efficacy, without departing from the teachings of the present invention.

The bladder of the air bag 62 preferably encloses air, $CO_2$, or a similar gas-like substance or, may alternatively enclose liquids or gels such as water, silicon or the like. Any such assembly may provide the desired deformability and consequent cushioning or energy storing, absorption and release characteristics.

As shown in FIGS. 1-6, ready control of the spring rate and performance of the ski leg 20 by the wearer is provided by a PVC or urethane tube 64 which is solvent/bonded or otherwise suitably attached to the bladder of the air bag 62 so as to be in fluid or gaseous communication with the interior of the bladder. A valve 66 in communication with the tube 64 may be provided to receive a needle from an air pump (not shown) or from a $CO_2$ cartridge (not shown), or may be adapted to receive other gases or fluids as is well known in the art. In one embodiment, the valve 66 is formed in the end of a small rigid cylinder 68 which is mounted transversely to the front side of the leg member 22 with a suitably strong fastening means (not shown). The air bag 62 may thus be quickly and easily inflated or deflated from the side of the ski leg 20 to provide the required level of pressure therein and vary the angle that the ski leg must be bent before the secondary stiffness member 34 contributes its bending resistance. Such a control allows the skier to adjust the performance of the ski leg 20 at will while on the slopes.

Various alternative methods for constructing the bladder of the air bag 62 are possible, including having a bifurcated or otherwise divided bladder to include separate fluid chambers. The bifurcation may be achieved by heat sealing a strip across a portion of the bladder, or may be fabricated in numerous other manners. Various shapes may be constructed (such as horseshoe shaped, W-shaped, etc.) and any beneficial number of chambers, which may or may not be in gaseous or fluid communication with one another, depending on the desired performance of the bladder, may be provided. For example, the heat sealed strip may be utilized to cause a tapering or reduction in cross-section along the length of the bladder to fit between the structural components of the ski leg 20. Such a tapering may also provide more desirable or more gradual cushioning effects than a nontapering bladder. Additionally, the provision of multiple chambers produces and even eliminates the problem of rollout of the air bag 62. Rather than providing only a central contact location between the air bag 62 and the secondary stiffness member 34 and ankle portion 36, respectively, separate chambers provide multiple contact surfaces distributed such that the points of contact are spread laterally from the longitudinal centerline of the prosthetic ski leg.

Function Block

Also seen in the embodiment of FIGS. 1-6, a rearward bending stiffness adjustor comprises a resilient function block 76 interposed between the rear surface of the ankle portion 36 and a tubular air bag 78 extending transversely through the function block. The function block 76 has a substantially wedge-shaped configuration and determines the lever arm of the ankle portion 36 in rearward bending while isolating the under surface of the ankle portion and the upper surface of the sole member 24 from each other. The function block 76 may be fabricated from a wide variety of resilient materials, including natural and synthetic rubbers, or the like. Furthermore, the function block 76 can be provided in different sizes and materials having different compression characteristics so that, respectively, the lever arm of the ankle portion 36 in rearward bending may be increased or decreased, respectively, and the rearward deflection of the ankle portion correspondingly increased or decreased. A greater length function block 76 reduces the lever arm of the ankle portion 36 and correspondingly reduces the modulus of deflection of the leg member 22, while a smaller length function block increases the lever arm and correspondingly increases the deflection of the leg member under load.

Tubular Air Bag

The tubular air bag 78 provides an adjustable stiffener within the function block 76 to control the timing and level of stiffness added to the ankle portion 36 in rearward bending. The tubular air bag 78 may be constructed of a similar manner as the front air bag 62 and may also include adjustment means such as a fluid transfer tube terminating in a valve at one end of a small cylinder 82 mounted transversely across the leg member 22 with a suitably strong fastening means (not shown). The air bag 78 may be epoxied or otherwise affixed in place within the function block 76 by any suitable means. There are thus two control means provided on the ski leg: one to adjust forward bending stiffness and the other to adjust rearward bending stiffness.

Naturally, the absence of the tubular air bag 78, analogous to no pressure in the air bag, would result in a cylindrical cavity through the function block 76 substantially reducing the compressive strength of the function block. Thus, with a sufficient rearward bending load applied, the cavity would collapse and the function block 76 would be simultaneously reduced in effective thickness, its natural resiliency applied to the ankle portion only when the cavity was fully collapsed. On the other hand, the air bag may be pressurized to provide a very stiff central core for the function block 76, substantially increasing its compressive strength. For instance, the tubular air bag 78 may be pressurized to 80 psi providing a relatively rigid central core for the function block 76 so that the volume of resilient material in the function block 76 in the regions between the air bag and the ankle portion 36 and between the air bag and the sole member 24 comprise the material to be compressed prior to the ankle member 36 substantially pivoting about a fulcrum generally defined by the stiff air bag. Thus, the fulcrum of the ankle portion 36 in rearward bending has been moved farther to the left in the drawings and the leg member 22 experiences substantial increase in stiffness in rearward bending.

Of course, the sizes and shapes of the function block 76 and tubular air bag 78 may be altered depending on the desired performance characteristics. For example, the function block may comprise a highly compressible material and only serve to position the tubular air bag 78 which provides the majority of bending resistance. Alternatively, the function block 76 may be constructed quite a lot larger than the tubular air bag 78 and the air bag thus would only provide a small change in stiffness depending on the internal pressure. Various combinations are possible within the scope of the present invention.

Non-Integral Secondary Stiffness Member

An alternative prosthetic ski leg 90 is shown in FIG. 7. The ski leg 90 comprises a leg member 92 connected to a sole member 94 and a secondary stiffness member 96. The leg member 92 and sole member 94 are attached together with a connector 98 at a portion proximate the toe end where both members run parallel and horizontal. A toe binding mount 100 and a heel binding mount 102 provide means for mounting the ski leg 90 to conventional bindings of a ski. An air bag 104 is provided between the secondary stiffness member 96 and an ankle portion 106 of the leg member 92. The air bag 104, in conjunction with the secondary stiffness member 96, provides a forward bending stiffness adjustor, similar to that described for the embodiment of FIGS. 1-6.

The prosthetic ski leg 90 of FIG. 7 resembles the prosthetic ski leg 20 of FIGS. 1-6 in many ways except for the provision of a separate secondary stiffness member 96. The secondary stiffness member may be epoxied or otherwise adhered to a rigid upper portion 93 of the leg member 92 or, alternatively, may be demountably attached with various types of fasteners (not shown). The secondary stiffness member 96 thus may be easily detached and replaced with a stiffer or more flexible piece to control the performance of the ski leg 90.

The ski leg 90 also includes a rearward bending stiffness adjustor 112 comprising a wedge-shaped resilient piece 108 with a tubular air bag 110 positioned therein. The rearward bending stiffness adjustor 112 is interposed between the rear surface of the ankle portion 106 and the sole member 94. The material and shape of the resilient function block are chosen to influence the stiffness of the ankle portion 106 in rearward bending while the air bag may be used to fine-tune the rearward stiffness with the ski leg 90 attached.

Shock Cord

In FIG. 8, a prosthetic ski leg 114 incorporating a shock cord 116 is shown. The prosthetic ski leg 114 comprises a leg member 118 extending downward and curving to meet a sole member 120, the members being attached at a connector 122. The ski leg 114 also includes front and rear binding mounts 124a, 124b, respectively. The shock cord 116 is fastened at one end to a hook or eye ring 126 mounted to the rear end of the sole member 120 or to the rear binding mount 124b. The shock cord 116 loops around the radius of an ankle portion 128 of the leg member 118 to impart a resistance to forward bending of the leg member. Alternatively, the shock cord 116 may be fastened to the rear side of the ankle portion 128 by any number of means.

The shock cord 116 may be fabricated from a resilient material or from a less pliant material such as steel cable. Preferably, the shock cord 116 is manufactured of a solid urethane rod having a hardness durometer of between 80 and 90 Schorr. As the leg member 118 bends forward, the shock cord 116 stretches to apply a force on the ankle portion 128 and resist any further forward bending. In the case of a solid urethane shock cord 116, if bending forward, the leg member encounters an increased resistance to bending and thus the shock cord functions as a secondary stiffness member. A number of different shock cords may be carried by an amputee skier and interchanged depending on the level of stiffness desired. This easy interchangeability provides a mechanism to control the performance of the ski leg 20 at will while on the slopes.

Preferably, the shock cord 116 provides a nonlinear addition of stiffness to the leg member 118 so that an initial resistance is encountered which stretches the shock cord until the shock cord reaches a fully stretched position, whereupon the shock cord will not stretch any further. Thus, the shock cord provides a limit to the amount of forward bending which the leg member 118 may experience. Alternatively, the shock cord 116 may have some slack initially to allow for a limited range of motion of the leg member 118 prior to the shock cord being pulled taut. In this instance, there is a delay in the application of elastic force of the shock cord 116. Alternatively, the shock cord 116 may be relatively non-elastic, such as steel cable, and simply function as a range of motion limiter.

A rearward bending stiffness adjustor 129, similar to the resilient function block 76 and the transversely embedded tubular air bag 78 of the embodiment shown in FIGS. 1-6, is interposed between the rear surface of the ankle portion 128 and the sole member 120. The resilient function block has a substantially wedge-shaped configuration and is chosen to influence the stiffness of the ankle portion 128 in rearward bending while the air bag may be used to fine-tune the rearward stiffness with the ski leg 114 attached.

In FIG. 9, a further embodiment of the prosthetic ski leg 130 is shown. The ski leg 130 comprises a leg member 136 connected to a sole member 137 and includes front and rear binding mounts 139a and 139b, respectively. The prosthetic ski leg 130 incorporates elements of the two previously described ski legs with a shock cord 132 extending around a secondary stiffness member 134. The shock cord 132 thus is stretched not by the leg member 136 but by the secondary stiffness member 134. On stretching of the shock cord 132, the second stiffness member 134 is pulled towards an air bag 138. After a predetermined angle of forward bending of the leg member 136, the shock cord 132 has pulled the secondary stiffness member 134 into the air bag 138 to combine and add a further level of stiffness to the ski leg 130. The air bag 138 may be provided with the aforementioned pressure adjusting means, such as the valve 140 and the shock cord 132 may be interchanged with a different shock cord, these features combining to provide a high level of adjustability of the stiffness of the prosthetic ski leg 130.

In an alternate embodiment (not shown), the shock cord 132 may loop around an ankle portion 142 of the leg member 136 to function in a similar manner as that shown in FIG. 7. Thus, the shock cord 132 imparts a stiffness force directly on the leg member 136, while the secondary stiffness member 134 also adds a level of stiffness depending on the inflation pressure of the air bag 138. These two features then complement each other and once again provide a high level of adjustability of the prosthetic leg stiffness.

A rearward bending stiffness adjustor 144, similar to the resilient function block 76 and the transversely embedded tubular air bag 78 of the embodiment shown in FIGS. 1-6, is interposed between the rear surface of the ankle portion 142 and the sole member 137. The resilient function block has a substantially wedge-shaped configuration and is chosen to influence the stiffness of the ankle portion 142 in rearward bending while the air bag may be used to fine-tune the rearward stiffness with the ski leg 130 attached.

Sole Connector

As shown in FIG. 10, the connector 150 between a leg member 152 and a sole member 154 provides a further means for adjusting the stiffness of a prosthetic ski leg 156. In this configuration, the connector, such as nut and bolt combination 150, passes through aligned longitudinal slots 158 in both the leg member and sole member. The connector 150 is loosened and slid forward or backward toward the toe or heel, respectively, of the prosthetic ski leg 156. Sliding the connector 150 towards a toe binding mount 160 provides a greater flexibility of leg member 152, as the rigid connection is moved further to the right of FIG. 10. Likewise, sliding the connector 150 rearward toward a heel binding mount 161 increases the stiffness of the leg member 152.

A rearward bending stiffness adjustor 162, similar to the resilient function block 76 and the transversely embedded tubular air bag 78 of the embodiment shown in FIGS. 1-6, is interposed between the rear sure, ace of the leg member 152 and the sole member 154. The resilient function block has a substantially wedge-shaped configuration and is chosen to influence the stiffness of the leg member 152 in rearward bending while the air bag may be used to fine-tune the rearward stiffness with the ski leg 156 attached.

C-Shaped Secondary Stiffness Member

A further embodiment of the prosthetic ski leg 164 is shown in FIG. 11. A leg member 166 and sole member 168 are connected as described above with a connector 170. An arcuate or C-shaped auxiliary or secondary stiffness member 172 attaches to the proximate center of the curvilinear ankle portion 174 with a fastener 173. Upon forward bending of the leg member 166, the outwardly diverging ends 176a, 176b of the stiffness member 172 meet the leg member and contribute to the stiffness thereafter. In this regard, the C-shaped secondary stiffness member 172 possesses a smaller radius of curvature than the ankle portion 174, the difference in radius of curvature determining the spacing between the ends 176a, 176b and the ankle portion which, in turn, determines the amount of bending of the leg member 176 prior to the C-shaped secondary stiffness member coming into play. Preferably, the C-shaped secondary stiffness member 172 is fabricated from a similar material as the leg member, but may also be manufactured of various other materials having lower fatigue life as the stiffness member is not a primary load bearing element. The stiffness member 172 is preferably fastened in the center to the proximate center of curvature of the ankle portion 174 with any number of fasteners including the nut and bolt combination 170 shown.

A rearward bending stiffness adjustor 177, similar to the resilient function block 76 and the transversely embedded tubular air bag 78 of the embodiment shown in FIGS. 1–6, is interposed between the rear surface of the ankle portion 174 and the sole member 168. The resilient function block has a substantially wedge-shaped configuration and is chosen to influence the stiffness of the ankle portion 174 in rearward bending while the air bag may be used to fine-tune the rearward stiffness with the ski leg 164 attached.

Other Embodiments

Figure 12:
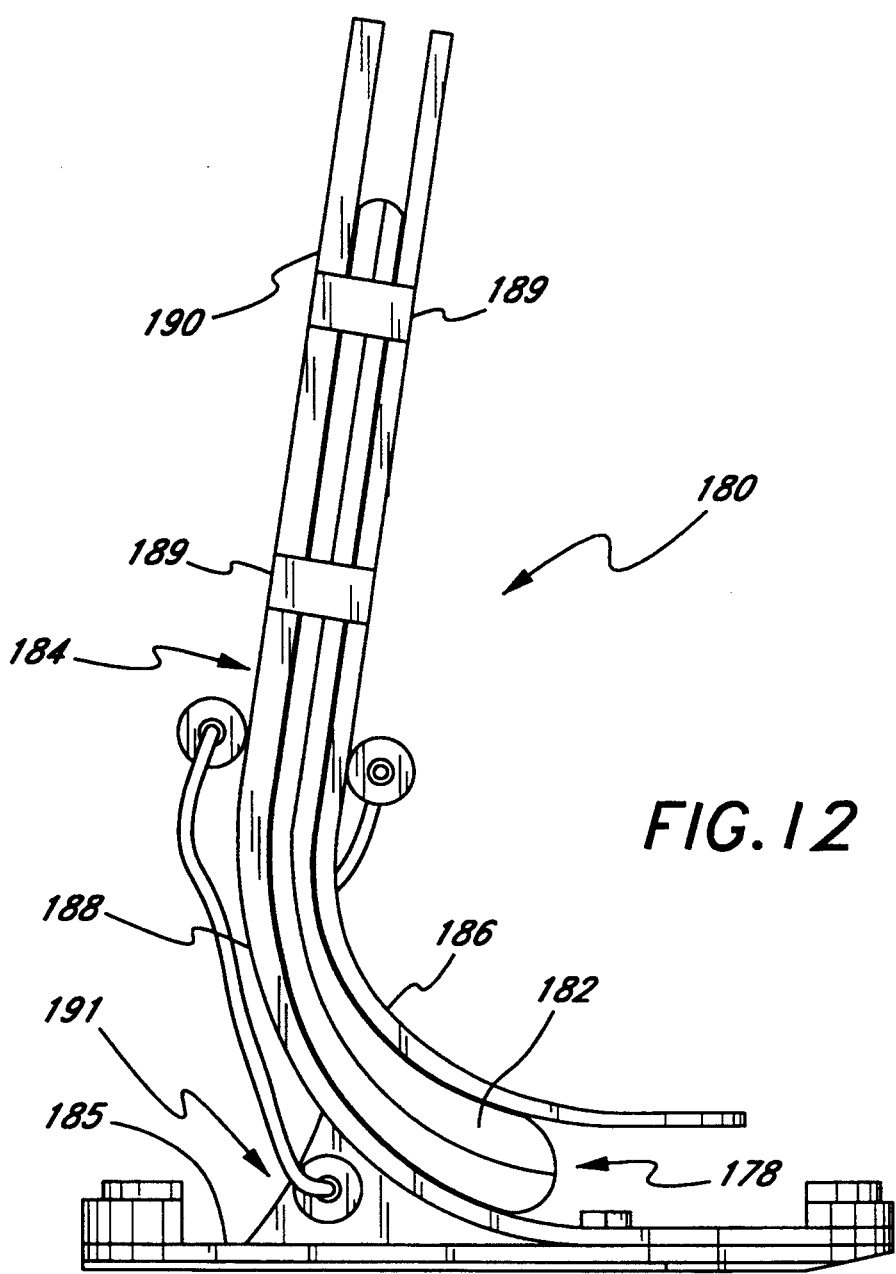
FIG. 12 is a side elevational view of a further alternative embodiment of the prosthetic ski leg of the present invention having a secondary stiffness member spaced from a leg member with a vertically disposed air bag therebetween acting as a forward bending stiffness adjustor.

In a further configuration, as shown in FIG. 12, a bending stiffness adjustor 178 extends substantially the entire height of a prosthetic ski leg 180. The bending stiffness adjustor may be in the form of an elongated air bag 182 which is sandwiched between a leg member 184 and a secondary stiffness member 186. The leg member 184 and secondary stiffness member 186 may be coupled at the top region with a stump connector (not shown) and also at locations further down towards an ankle portion 188 of the leg member with straps 189 or other means. Inflation and deflation of the air bag 182 increases or decreases, respectively, the forward and rearward bending stiffness of the prosthetic ski leg all the way from the ankle portion 188 upward into the straight leg portion 190.

An auxiliary rearward bending stiffness adjustor 191, similar to the resilient function block 76 and the transversely embedded tubular air bag 78 of the embodiment shown in FIGS. 1–6, is interposed between the rear surface of the ankle portion 188 and a sole member 185. The resilient function block has a substantially wedge-shaped configuration and is chosen to influence the stiffness of the ankle portion 188 in rearward bending while the air bag may be used to fine-tune the rearward stiffness with the ski leg 180 attached.

Figure 13:
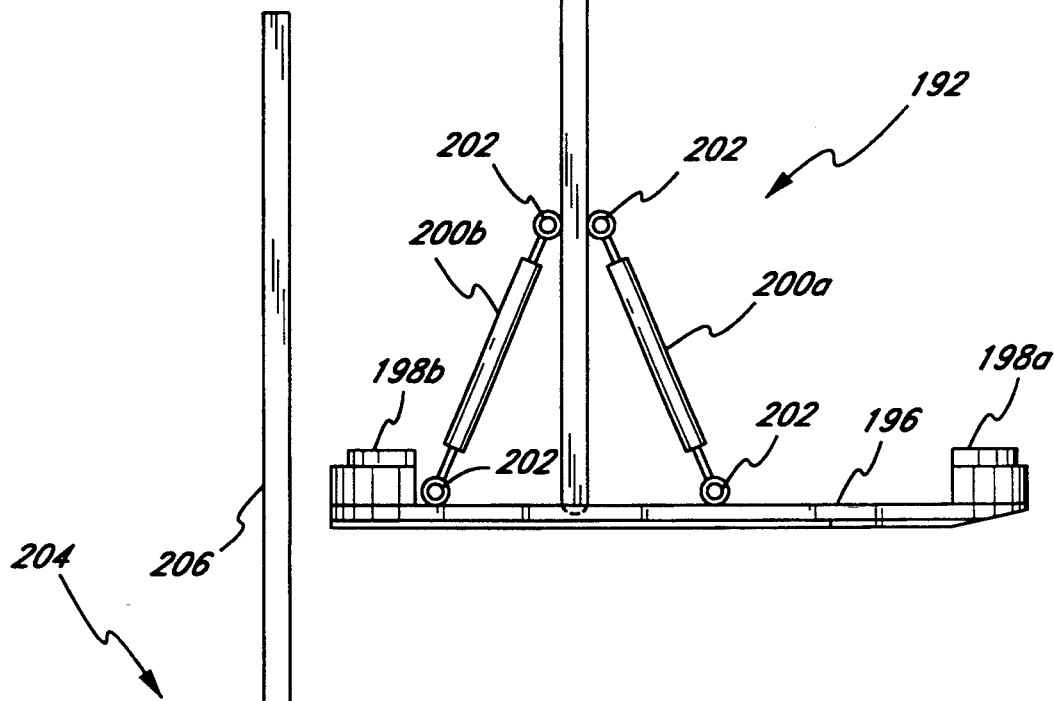
FIG. 13 is a side elevational view of a further alternative embodiment of the prosthetic ski leg showing a pair of shock absorbers attached to both sides of a leg member acting as both forward and rearward bending stiffness adjustors.

With reference to FIG. 13, a prosthetic ski leg 192 comprises a generally elongate leg member 194 coupled at a lower end to a sole member 196 having toe and heel binding mounts 198a, 198b and a pair of bending stiffness adjustors 200a, 200b. The bending stiffness adjustors 200a, 200b are pivotally coupled by hinges 202 at points on either side of the leg member 194 and on top of the sole member 196. The leg member 194 may be formed integral with the sole member 196, or may be rigidly attached during assembly. Preferably, the leg member 194 and sole member 196 are joined at a location and in an orientation which mirrors a center line through a typical leg, ankle, and foot. Specifically, the bottom end of the leg member 194 is preferably attached to a point proximate the heel binding mount 198 of the sole member 196 and extends upward at a small angle, preferably approximately 10°.

The bending stiffness adjustors may be shock absorbers 200a, 200b which serve to augment the stiffness of the attachment point between the leg member and sole member. The shock absorbers may be adjustable to vary the damping resistance. In this regard, the leg member 194 may be made quite a bit thicker at the bottom portion and be attached to the sole member in a manner capable of withstanding the shock loading and fatigue of a typical ski leg. However, in the present invention, the leg member 194 has sufficient thickness and strength at the connection with the sole member 196 to withstand such forces when combined with the supporting shock absorbers 200a, 200b. The shock absorbers 200a, 200b provide a damping resistance to bending of the leg member 194 which slows down the rate of bending. Depending on the material and inherent stiffness, the resilient leg member 194 may then spring back to its original orientation. Alternatively, and as is well known in the art, coil springs may be provided within the shock absorbers 200a, 200b to enhance the rate of return to an original orientation.

Figure 14:
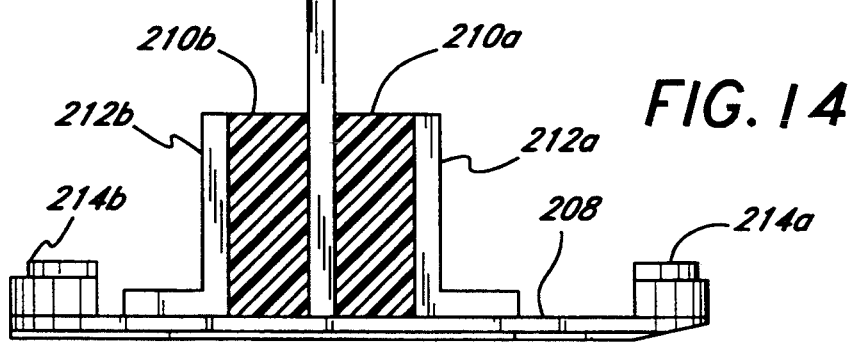
FIG. 14 is a side elevational view of a further alternative embodiment of the prosthetic ski leg with a pair of air bags sandwiched around a leg member by a pair of L-shaped brackets, the air bags acting as forward and rearward bending stiffness adjustors.

In a still further embodiment of the present invention, a prosthetic ski leg 204 is shown in FIG. 14. The prosthetic ski leg 204 comprises an upstanding leg member 206 mounted at the lower end in a rigid manner to a sole member 208. A pair of resilient bumpers or cushions 210a, 210b are braced by a pair of brackets 212a, 212b on either side of the leg member 206. The bumpers 210a, 210b may also be air bags having valves which provide a level of stiffness adjustment. A stump connector (not shown) is fastened to the top end of the leg member 206 and the prosthetic ski leg 204 includes front and rear binding mounts 214a, 214b for connection to the bindings of a ski.

Although this invention has been described in terms of certain preferred embodiments, other embodiments that are apparent to those of ordinary skill in the art are also within the scope of this invention. Accordingly, the scope of the invention is intended to be defined only by the claims.

I claim:

1. A prosthetic ski leg for use by an amputee, said leg being adapted to be secured directly to a ski for use in skiing, comprising:
   a leg portion for extending downwardly from said amputee to support said amputee;
   an ankle portion; and
   a prosthetic foot portion extending from a heel portion to a forward toe portion, said foot portion having ski binding mounts positioned directly on said foot portion so as to avoid the need for a ski boot, one binding mount being located on said heel portion and another binding mount being located on said toe portion, said binding mounts functioning to mount said prosthetic ski leg to ski bindings.

2. The prosthetic ski leg of claim 1, wherein said leg portion is substantially rigid and said ankle portion is flexibly curved downward and forward, wherein said ankle portion determines the stiffness in bending of said prosthetic ski leg.

3. The prosthetic ski leg of claim 2, further comprising a secondary stiffness member rigidly joined to said leg portion, said secondary stiffness member extending over said ankle portion, wherein said secondary stiffness member provides additional stiffness to said prosthetic ski leg.

4. The prosthetic ski leg of claim 3, wherein a second resilient member is interposed between said secondary stiffness member and said leg portion and/or said ankle portion, said second resilient member cooperating with said secondary stiffness member to adjustably determine the extent to which said leg portion bends forward relative to said foot portion.

5. The prosthetic ski leg of claim 4, wherein said second resilient member is a fluid filled bag.

6. The prosthetic ski leg of claim 5, wherein said bag includes means for adjusting internal pressure.

7. The prosthetic ski leg of claim 5, wherein said fluid is air.

8. The prosthetic ski leg of claim 1, further comprising a resilient member positioned between said ankle portion and said foot portion to control the rearward bending of said leg portion with respect to said foot portion.

9. The prosthetic ski leg of claim 8, wherein said resilient member is a wedge-shaped member positioned adjacent an interconnection of said ankle portion and said foot portion.

10. The prosthetic ski leg of claim 9, wherein a tubular air bag is disposed transversely through a cavity in said resilient member, said air bag having valve means for adjusting the pressure therein.

11. The prosthetic ski leg of claim 1, further comprising a flexible member to control the forward bending of said leg portion with respect to said foot portion.

12. The prosthetic ski leg of claim 3, wherein one or more restraining straps are mounted to said foot portion and engaged with said secondary stiffness member limiting the separation of said foot portion and said secondary stiffness member.

13. The prosthetic ski leg of claim 1, further comprising a flexible cord extending from said foot portion and around said ankle portion, wherein said cord resists the forward bending of said leg portion relative to said foot portion.

14. The prosthetic ski leg of claim 13, wherein said cord is flexibly elastic.

15. The prosthetic ski leg of claim 13, wherein said cord is relatively inelastic, wherein the forward bending of said leg portion is limited by the length of said cord.

16. A prosthetic ski leg for an amputee, comprising:
a substantially rigid leg portion;
an ankle portion extending downward and forward from said leg portion, said ankle portion being relatively flexible in a vertical plane parallel to the fore and aft direction, said ankle portion being relatively stiff in bending in other planes or in torsion; and
a prosthetic foot portion extending from a rearward heel section to a forward toe section, said heel ski section having a heel binding mount attached thereto and said toe section having a toe ski binding mount attached thereto, wherein said toe and heel ski binding mounts function to secure said prosthetic ski leg directly to ski bindings wherein the need for a ski boot is eliminated.

17. The prosthetic ski leg of claim 16, wherein said prosthetic ski leg is made of graphite fiber embedded in epoxy resin.

18. The prosthetic ski leg of claim 16, further comprising an auxiliary member extending along a forward side of said leg portion and/or said ankle portion, said auxiliary member providing additional stiffness to prevent excessive forward bending of said leg portion with respect to said foot portion.

19. The prosthetic ski leg of claim 18, further comprising a resilient member positioned adjacent said auxiliary member and said leg portion and/or ankle portion, said resilient member adjustably determining the flexibility of said prosthetic ski leg in said vertical plane.

20. The prosthetic ski leg of claim 19, wherein said resilient member comprises a bladder, said bladder having an air tube and valve for adjusting the pressure therein, wherein the stiffness of said prosthetic ski leg in the forward bending direction can be increased by increasing the pressure in said bladder, and said stiffness of said prosthetic ski leg can be decreased by decreasing the pressure in said bladder.

21. The prosthetic ski leg of claim 16, wherein a shock cord is provided to prevent the excessive forward bending of said prosthetic ski leg in said vertical plane.

22. The prosthetic ski leg of claim 16, further comprising a resilient wedge-shaped member positioned adjacent an interconnection of said ankle portion and said foot portion, said resilient wedge-shaped member adjustably determining the rearward bending stiffness in said vertical plane of said prosthetic ski leg.

23. The prosthetic ski leg of claim 16, wherein the relative position of said ankle portion with respect to said foot portion is adjustable.

24. The prosthetic ski leg of claim 16, wherein said foot portion is demountably secured to said ankle portion.

25. The prosthetic ski leg of claim 16, wherein a C-shaped member is positioned on the forward side of said ankle portion to resist the forward bending of said leg portion.

26. The prosthetic ski leg of claim 16, wherein said flexibility is resisted by shock absorbing members.

27. The prosthetic ski leg of claim 16, wherein said flexibility is resisted by resilient members.

28. A prosthetic foot for use by an amputee, said prosthetic foot being adapted to be secured directly to a ski for use in skiing, comprising:
a prosthetic foot member extending from a rearward heel section to a forward toe section, said foot member adopted to be operatively secured to the amputee's stump, wherein a first ski binding mount is secured to said heel section, and a second ski binding mount is secured to said toe section, said binding mounts functioning to secure said prosthetic foot directly to ski bindings such that the need for a ski boot to secure said prosthetic foot to a ski is eliminated.

29. The prosthetic foot of claim 28, wherein each of said binding mounts are separately formed and secured to the upper side of said foot member such that ski bindings can be utilized to clamp said foot member securely to a ski.

30. The prosthetic foot of claim 28, wherein said foot member is secured to a lower end of a pylon member, wherein the pylon member is configured to extend from the foot member to the amputee's stump, said pylon member having an ankle section being relatively flexible in the vertical plane parallel to the fore and aft direction.

31. The prosthetic foot of claim 28, wherein said foot member extends horizontally along substantially a horizontal plane.

32. The prosthetic foot of claim 31, wherein a substantially curved and planar ankle section is configured to extend downward and forward from the amputee's stump.

33. The prosthetic foot of claim 32, wherein a substantially vertically oriented pylon member is configured to extend between said stump of said amputee and said ankle section such that said pylon member supports said amputee relative to a ground surface.

* * * * *